(12) United States Patent
Yamamoto et al.

(10) Patent No.: US 9,013,693 B2
(45) Date of Patent: Apr. 21, 2015

(54) PARTICLE ANALYZER, OPTICAL SYSTEM FOR PARTICLE ANALYZER, AND LENS FOR PARTICLE ANALYZER

(71) Applicant: Sysmex Corporation, Kobe-shi, Hyogo (JP)

(72) Inventors: Takeshi Yamamoto, Kobe (JP); Seiichiro Tabata, Kobe (JP)

(73) Assignee: Sysmex Corporation, Kobe-Shi, Hyogo (JP)

( * ) Notice: Subject to any disclaimer, the term of this patent is extended or adjusted under 35 U.S.C. 154(b) by 0 days.

(21) Appl. No.: 14/209,322

(22) Filed: Mar. 13, 2014

(65) Prior Publication Data

US 2014/0293281 A1    Oct. 2, 2014

(30) Foreign Application Priority Data

Mar. 26, 2013    (JP) ................................. 2013-064546

(51) Int. Cl.
*G01N 21/00*    (2006.01)
*G01N 21/53*    (2006.01)
*G01N 15/14*    (2006.01)
*G01N 15/10*    (2006.01)

(52) U.S. Cl.
CPC .......... *G01N 21/53* (2013.01); *G01N 2015/144* (2013.01); *G01N 2015/1006* (2013.01); *G01N 15/1459* (2013.01); *G01N 15/1434* (2013.01)

(58) Field of Classification Search
USPC ........... 356/335–341, 72–73, 246; 250/458.1, 250/216
See application file for complete search history.

(56) References Cited

U.S. PATENT DOCUMENTS

| | | | |
|---|---|---|---|
| 2002/0141902 A1* | 10/2002 | Ozasa et al. | 422/82.09 |
| 2008/0024758 A1 | 1/2008 | Tabata | |
| 2008/0079929 A1* | 4/2008 | Luo et al. | 356/73 |
| 2008/0106736 A1* | 5/2008 | Graves et al. | 356/338 |
| 2008/0241911 A1* | 10/2008 | Ueno et al. | 435/287.1 |
| 2010/0165325 A1* | 7/2010 | Tabata | 356/39 |
| 2010/0177305 A1* | 7/2010 | Chen | 356/246 |

FOREIGN PATENT DOCUMENTS

JP    02-304332 A    12/1990

\* cited by examiner

*Primary Examiner* — Sang Nguyen
(74) *Attorney, Agent, or Firm* — Brinks Gilson & Lione

(57) ABSTRACT

A particle analyzer comprises a light source, a flow cell, an irradiating optical system, and a light receiving optical system. The light receiving optical system comprises a light focusing lens system which includes a light focusing lens configured to focus forward scattered light from the particles, a light receiving member configured to receive the forward scattered light, and a beam stopper. The beam stopper is provided in the light path between the light focusing lens system and the light receiving member. The light focusing lens has an aspheric lens form. The light focusing lens system is configured such that the focal distance of the forward scattered light through the central area which includes the optical axis is longer than the focal distance of the forward scattered light through the peripheral area outside the central area.

10 Claims, 12 Drawing Sheets

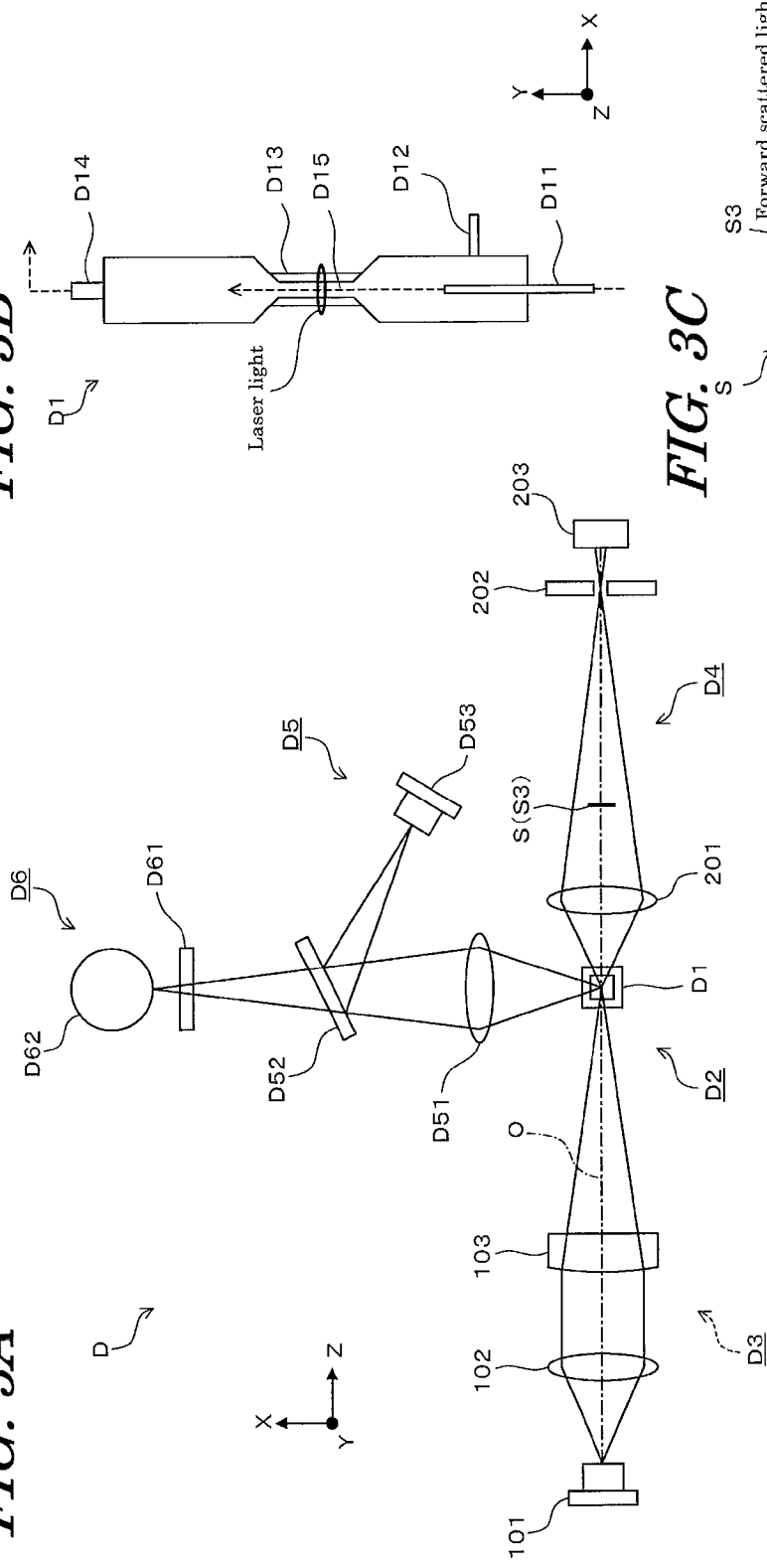
FIG. 3A
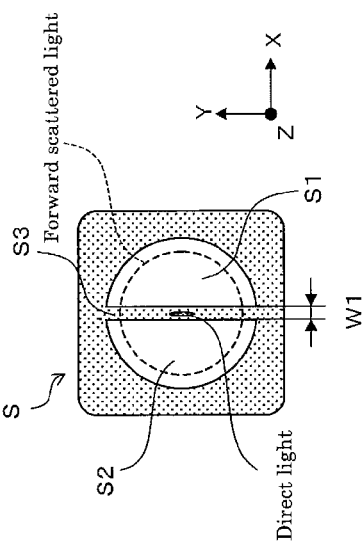
FIG. 3B
FIG. 3C

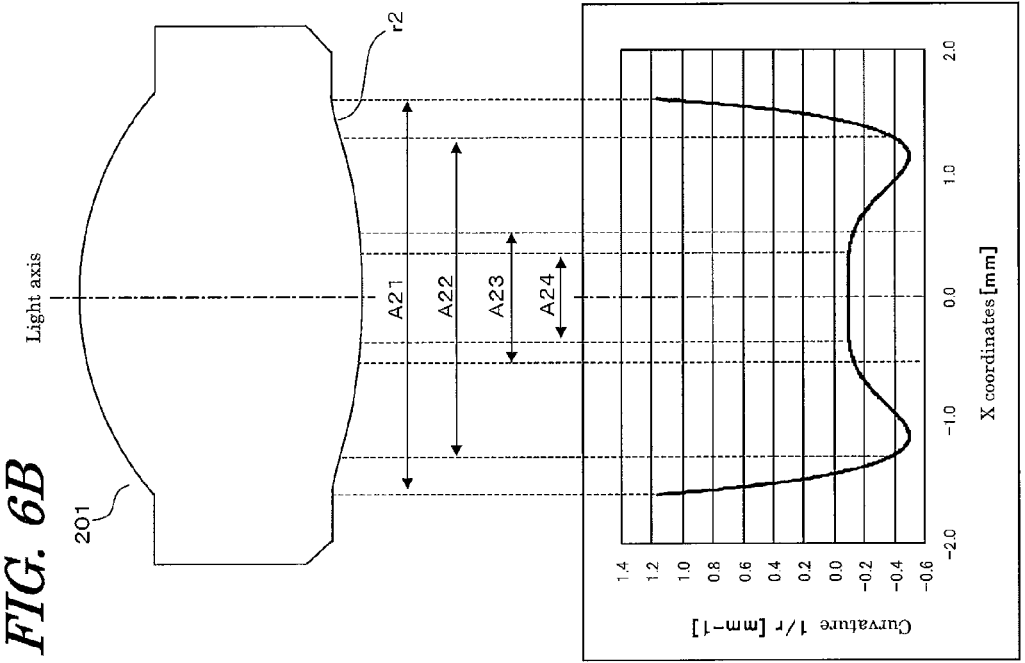
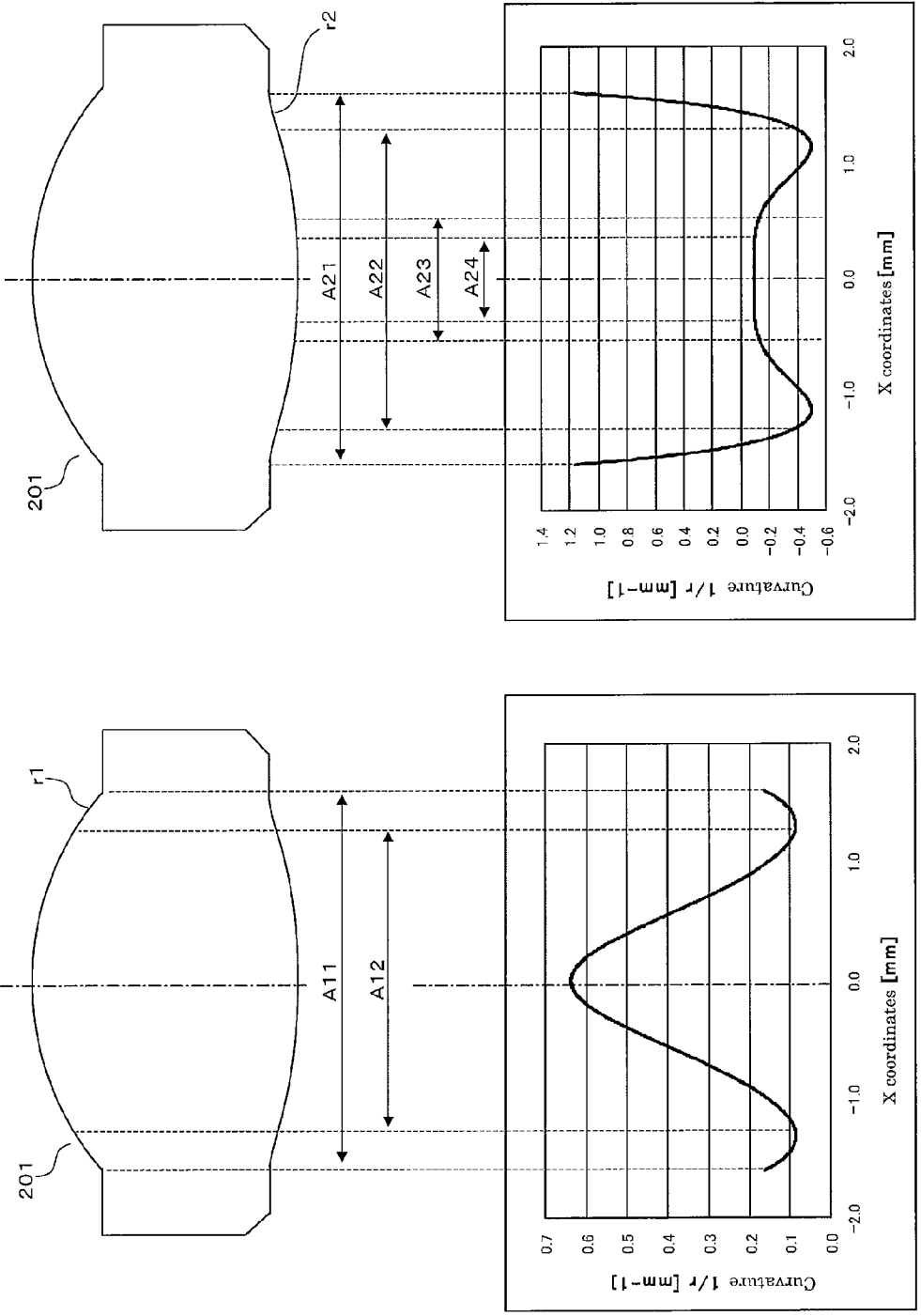
FIG. 6A
FIG. 6B

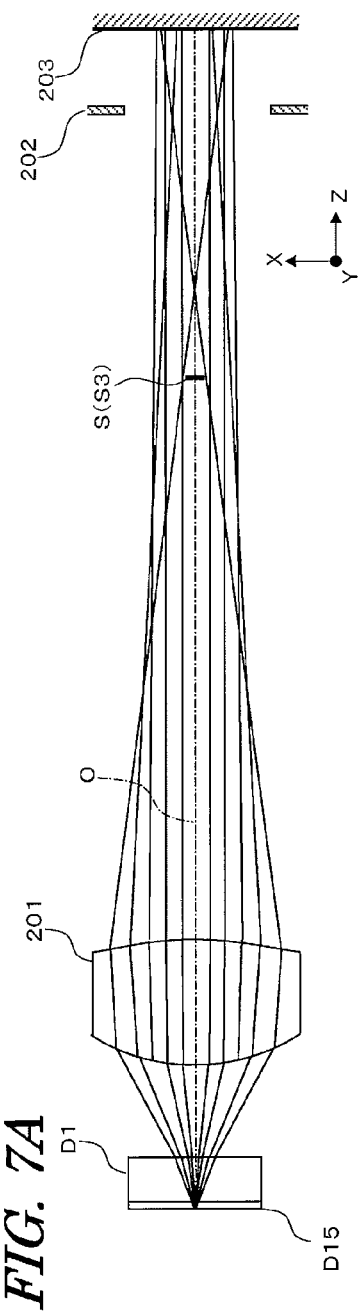
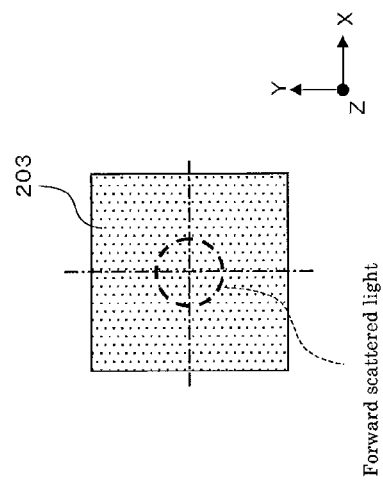
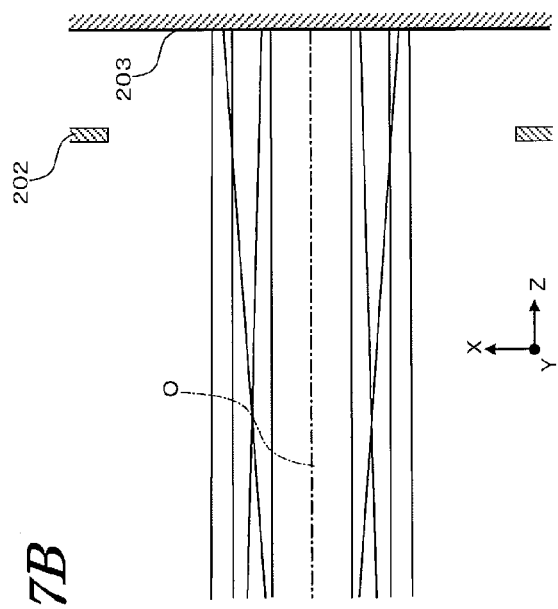
FIG. 7A
FIG. 7C
FIG. 7B

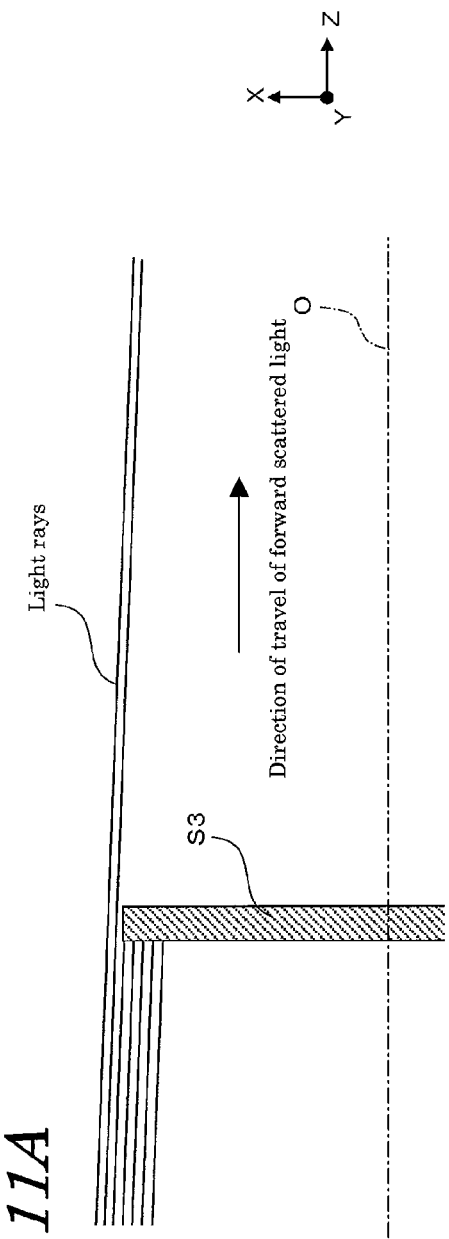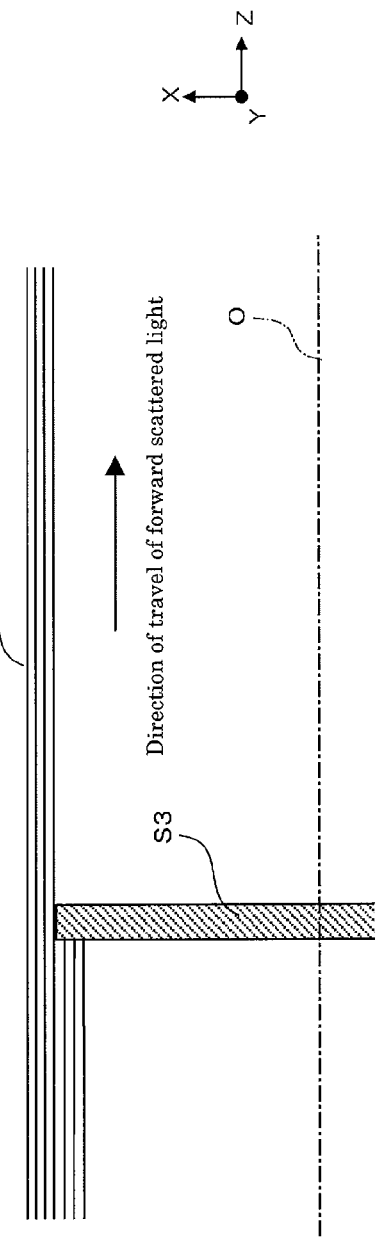

PARTICLE ANALYZER, OPTICAL SYSTEM FOR PARTICLE ANALYZER, AND LENS FOR PARTICLE ANALYZER

RELATED APPLICATIONS

This application claims priority under 35 U.S.C. §119 to Japanese Patent Application No. 2013-064546 filed on Mar. 26, 2013, the entire content of which is hereby incorporated by reference.

FIELD OF THE INVENTION

The present invention relates to a particle analyzer for analyzing particles contained in a flow irradiated by light, an optical system used in the particle analyzer, and a lens used to condense the light emanating from the particles onto a light receiving unit in a particle analyzer.

BACKGROUND OF THE INVENTION

Conventional particle analyzers using optical-type flow cytometers are well known. In this type of particle analyzer, a sample containing particles such as blood or the like flows through the flow cell and light from a light source is irradiated on the flow channel. The light from the particles is detected, and the type and number of particles are determined based on the detected light.

When the flow cell is irradiated by the light from the light source, the light is scattered by the particles flowing through the flow cell. Among all the scattered light, the light which scatters in the forward direction (forward scattered light) is focused on the light receiving surface of the light detecting unit via the light focusing lens. The forward scattered light is used to detect the feature quantities, that is, size, morphological information and the like, of the particles.

The direct light transmitted from the light source through the flow cell must be eliminated in order for the light detecting unit to detect the forward scattered light. Therefore, a beam stopper for blocking direct light is arranged within the light receiving optical system. Japanese Laid-Open Patent Application No. H02-304332 discloses a beam stopper arranged in the optical path between a light focusing lens and a light detecting unit.

When the beam stopper is deployed in this way, part of the forward scattered light, in addition to the direct light, is eliminated by the beam stopper. Hence, there is a need to reduce as much as possible the amount of forward scattered light eliminated by the beam stopper.

SUMMARY OF THE INVENTION

The scope of the present invention is defined solely by the appended claims, and is not affected to any degree by the statements within this summary.

A first aspect of the present invention is a particle analyzer comprising a light source, a flow cell configured to flow a sample which includes particles, an irradiating optical system configured to irradiate light from the light source to a flow channel inside the flow cell, and a light receiving optical system configured to receive light from the flow channel. The light receiving optical system comprises a light focusing lens system which includes a light focusing lens configured to focus forward scattered light from the particles that flow in the flow channel, a light receiving member configured to receive the forward scattered light which is focused by the light focusing lens system, and a beam stopper configured to block direct light from the light source, wherein the beam stopper is provided in the light path between the light focusing lens system and the light receiving member. The light focusing lens has an aspheric lens form. The light focusing lens system is configured such that the focal distance of the forward scattered light through the central area which includes the optical axis is longer than the focal distance of the forward scattered light through the peripheral area outside the central area.

A second aspect of the present invention is an optical system for a particle analyzer comprising an irradiating optical system configured to irradiate light from a light source to a flow channel in a flow cell through which a sample containing particles flows, a light receiving optical system configured to receive light from the flow cell. The light receiving optical system comprises a light focusing lens system which includes a light focusing lens configured to focus forward scattered light from the particles that flow in the flow channel, a light receiving member configured to receive the forward scattered light which is focused by the light focusing lens system, and a beam stopper configured to block direct light from the light source, wherein the beam stopper is provided in the light path between the light focusing lens system and the light receiving member. The light focusing lens has an aspheric lens surface. The light focusing lens system is configured such that the focal distance of the forward scattered light through the central area which includes the optical axis is longer than the focal distance of the forward scattered light through the peripheral area outside the central area.

A third aspect of the present invention is a lens for a particle analyzer which focuses forward scattered light from particles flowing in a flow channel on a light receiving surface of a light detecting unit by irradiating light on the flow channel in the flow cell. The lens comprises an aspheric lens surface. The focal distance of the central area is longer than the focal distance of the peripheral area.

BRIEF DESCRIPTION OF THE DRAWINGS

FIG. 3A schematically shows the structure of an optical detector;

FIG. 3B schematically shows the structure of a flow cell;

FIG. 3C schematically shows the structure of a beam stopper;

FIG. 6A shows the curvatures of the entrance surface of the forward light focusing lens of the example.

FIG. 6B shows the curvatures of the exit surface of the forward light focusing lens of the example;

FIG. 7A shows the condition of the forward scattered light focused by the forward light focusing lens;

FIG. 7B is an enlargement of the vicinity of the photodiode;

FIG. 7C shows the condition of forward scattered light irradiation on the light receiving surface of the photodiode;

FIG. 11A shows the condition of the light rays passing through the vicinity of the edge of the light shield of the beam stopper;

FIG. 11B shows the condition of the light rays passing through the vicinity of the edge of the light shield of the beam stopper.

DETAILED DESCRIPTION OF THE PREFERRED EMBODIMENTS

Figure 1:
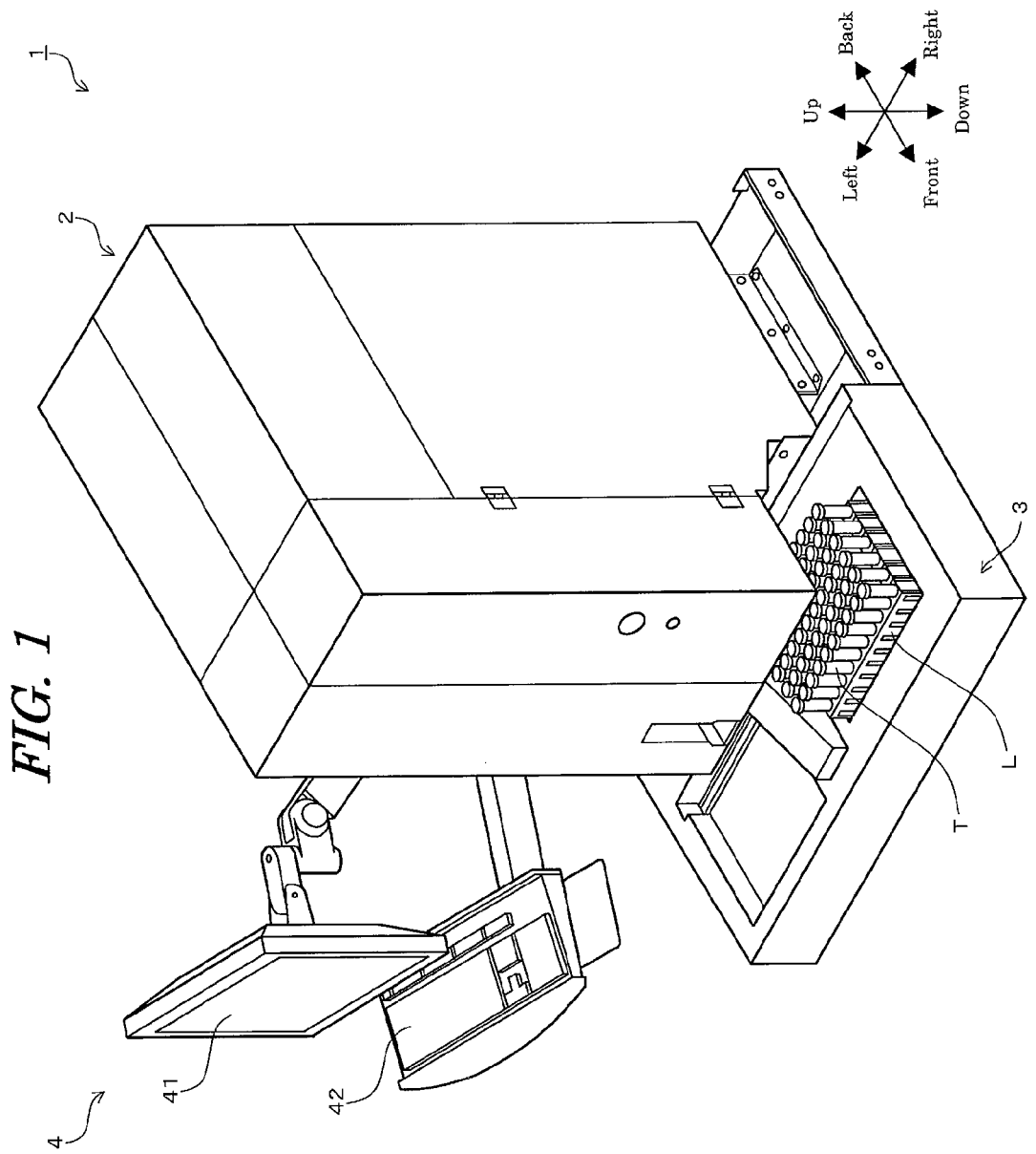
FIG. 1 is a perspective view showing an external view of an embodiment of a blood cell analyzing apparatus.

The preferred embodiments of the present invention will be described hereinafter with reference to the drawings.

The present embodiment applies the invention to a blood cell analyzer for performing examinations and analysis of blood, and to the light irradiating optical system of same. The blood cell analyzer of the embodiment is described below referring to the drawings.

FIG. 1 is a perspective view showing an external view of an embodiment of a blood cell analyzing apparatus.

The blood cell analyzer 1 is a multifunction blood cell analyzer which detects and counts white blood cells, red blood cells, and platelets contained in blood samples. The blood cell analyzer 1 is configured by a measuring unit 2, transporting unit 3 arranged on the front side of the measuring unit 2, and an information processing unit 4. A blood sample of peripheral blood collected from a patient is put in a sample container (collection tube) T. A plurality of sample containers T are held in a sample rack L, and the sample rack L is transported by the transporting unit 3 to deliver the blood samples to the measuring unit 2.

The information processing unit 4 has a display part 41 and an input part 42, and is connected to the measuring unit 2, transporting unit 3, and a host computer 5 (refer to FIG. 2) so as to be capable of communication therewith. The information processing unit 4 controls the operation of the transporting unit 2 and the measuring unit 3, performs analysis based on the measurement results of the measuring unit 3, and transmits the analysis results to the host computer 5 (refer to FIG. 2). The information processing unit 4 is configured by a personal computer.

Figure 2:
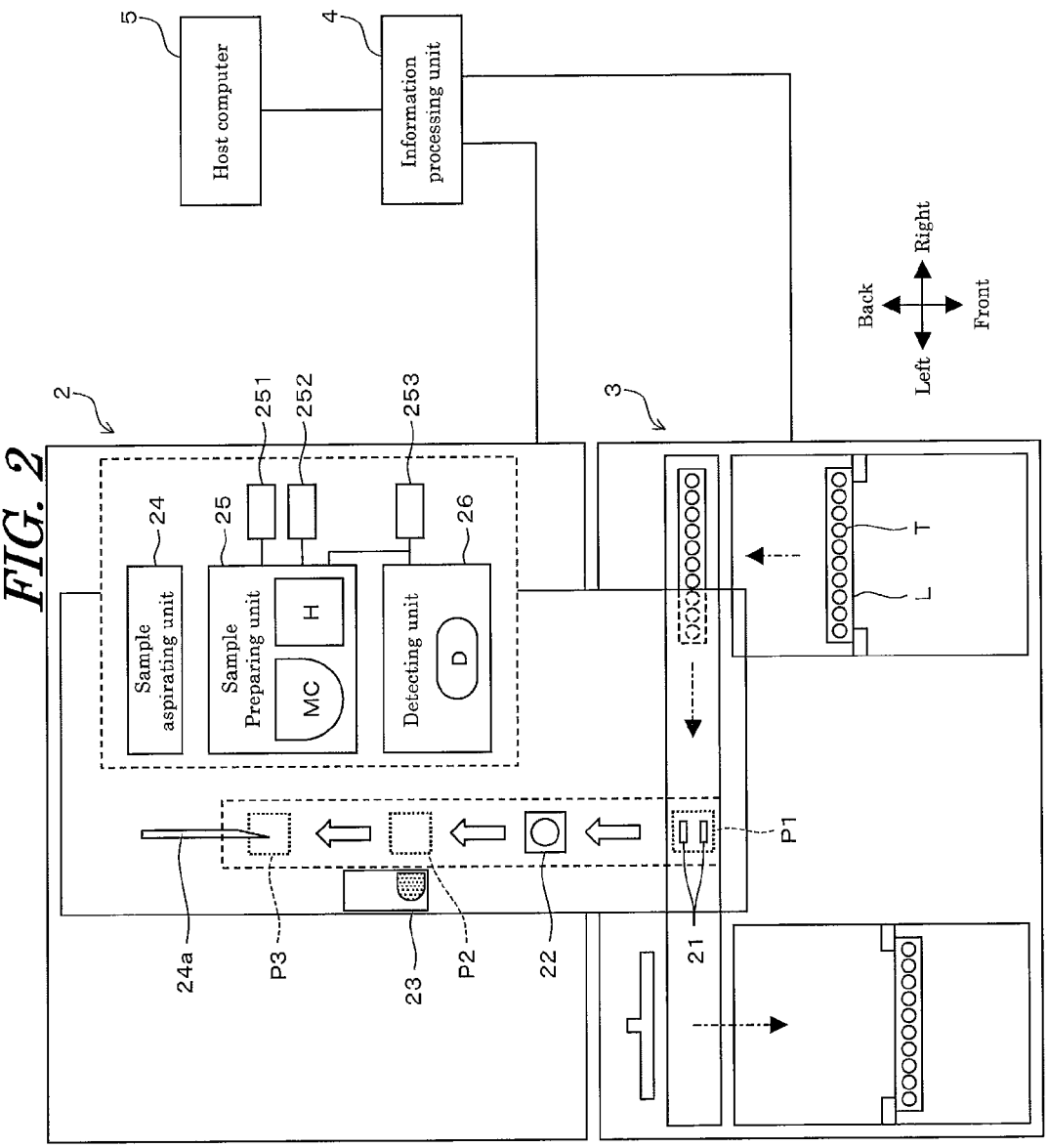
FIG. 2 schematically shows the structure of the measuring unit of the embodiment.

FIG. 2 schematically shows the structure of a measuring unit 2.

The measuring unit 2 is configured by a hand part 21, sample container setting part 22, barcode unit 23, sample aspirating part 24, sample preparing part 25, and detecting part 26. The sample aspirating part 24 has a piercer 24a for aspirating the sample from the sample container T. The sample preparing part 25 has a mixing chamber MC and a heater H, and prepares a measurement sample to use in measurements by mixing a sample and reagent. The detecting part 26 has an optical detector D to detect blood cells from the measurement sample. Each part of the measuring unit 2 is controlled by the information processing unit 4.

The sample container T, which is set at position P1 by the transporting unit 3, is gripped by the hand part 21 and lifted upward from the sample rack L. The sample within the sample container T is then mixed by shaking the hand part 21. Using the hand part 21, the mixed sample container T is set in the sample container setting part 22 which is disposed at the position P1. Thereafter, the sample container T is transported to the position P2 by the sample container setting part 22.

When the sample container T is set at the position P2, the barcode reader 23 arranged near position P2 reads the sample number from the barcode label adhered to the sample container T. Thereafter, the sample container T is transported to the position P3 by the sample container setting part 22. When the sample container T is set at position P3, a predetermined amount of sample is aspirated from the sample container T through the piercer 24a of the sample aspirating part 24. When sample aspiration is completed, the sample container T is transported forward by the sample container setting part 22 and returned to the holding position in the original sample rack L by the hand part 21. After the piercer 24a is moved to the position of the mixing chamber MC, a predetermined amount of the sample aspirated through the piercer 24a is discharged into the mixing chamber MC by the sample aspirating part 24.

The sample preparing part 25 is connected through a tube to a first reagent container 251 which contains a first reagent, a second reagent container 252 which contains a second reagent, and a reagent container 253 which contains a sheath fluid (diluting liquid). The sample preparing part 25 also is connected to a compressor (not shown in the drawings) which produces a pressure to apportion the respective reagents from the reagent containers 251 through 253. The sample preparing part 25 mixes the blood sample and the reagent in the mixing chamber MC, and heats the mixture for a predetermined time by a heater H to prepare a measurement sample. The measurement sample prepared by the sample preparing part 25 is supplied to the optical detector D of the detection part 26.

The detection part 26 is connected via a tube to the reagent container 253 which contains the sheath fluid (diluting liquid). The detection part 26 also is connected to a compressor (not shown in the drawings) which produces a pressure to apportion the sheath fluid (diluting liquid) from the reagent container 253.

FIG. 3A schematically shows the structure of an optical detector D. For the sake of convenience, the mutual intersection of the XYZ axes is shown in FIG. 3A. The X-axis direction is the vertical direction on the drawing sheet, and the Z-axis direction is the lateral direction on the drawing sheet. FIG. 3B schematically shows the structure of a flow cell D1. FIG. 3C schematically shows the structure of a beam stopper S.

Referring now to FIG. 3A, the optical detector D has a flow cell D1, a sheath flow system D2, an irradiation optical system D3, a forward scattered light receiving optical system D4, side scattered light receiving optical system D5, and fluorescent light receiving optical system D6.

The sheath flow system D2 is configured to feed the measurement sample within the flow cell D1 while encapsulated in sheath fluid to generate a flow within the flow cell D1. As shown in FIG. 3B, the flow cell D1 has a sample nozzle D11 for injecting a measurement sample upward toward an aperture part D13, a sheath fluid supply port D12, and a waste port D14. A flow path D15 of flowing measurement sample is formed within the aperture part D13.

The irradiating optical system D3 includes a semiconductor laser 101, a collimator lens 102, and a beam shaping lens 103.

Figure 5:
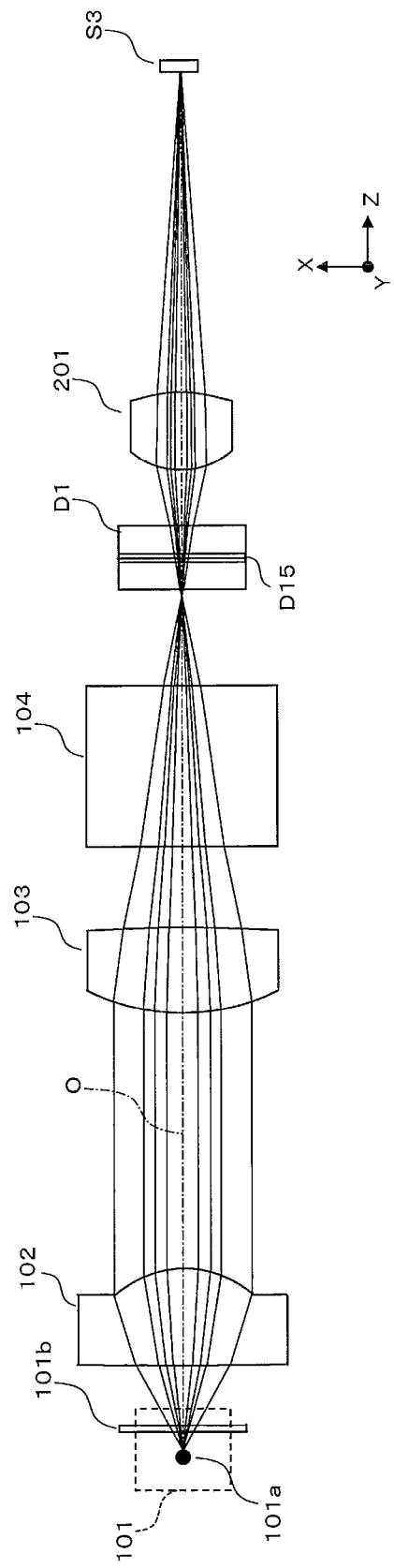
FIG. 5 shows the structures of the light irradiating optical system and the forward scattered light receiving optical system of an example.

The semiconductor laser 101 is arranged so that the stacking direction of the semiconductor layers of the emitter 101a (refer to FIG. 5 matches the X-axis direction. Accordingly, the angle of spread of the laser light emitted from the semiconductor laser 101 is maximum in the X-axis direction and minimum in the Y-axis direction. The semiconductor laser 101 emits laser light of a predetermined wavelength (642 nm in the present embodiment) in the Z-axis direction. The axial center of the laser light (optical axis) emitted form the semiconductor laser 101 matches the optical axis O of the optical system configured by the irradiating optical system D3 and the forward scattered light receiving optical system D4.

The collimator lens 102 converts the laser light emitted from the semiconductor laser 101 to parallel rays. The beam shaping lens 103 focuses the laser light transmitted through the collimator lens. The beam shaping lens 103 has an entrance surface with a curvature in both the X-axis and Y-axis directions, and an exit surface with a curvature in only the X-axis direction. The beam shaping lens 103 converges the laser light in the Y-axis direction to focus on a flow channel D15 (refer to FIG. 3B) of the flow cell D1, or converges the laser light in the X-axis direction to focus the laser light at a position in front (Z-axis negative side) of the flow channel D15. Accordingly, the light converged in the X-axis direction by the beam shaping lens 103 reaches from the focus position to the position of the flow channel D15 and spreads. The laser light therefore irradiates the flow channel D15 with a narrow beam shape in the X-axis direction as shown in FIG. 3B.

The forward scattered light receiving optical system D4 is configured by a forward light focusing lens 201, a beam stopper S, a pinhole 202, and a photodiode 203. Scattered light (forward scattered light) traveling from the flow cell D1 in the forward (Z-axis positive direction) is focused at the position of the pinhole 202 by the forward light focusing lens 201, then passes through the pinhole 202 and impinges by the photodiode 203. The photodiode 203 outputs electrical signals (forward scattered light signals) corresponding to the intensity of the received forward scattered light.

Among the laser light irradiating from the flow cell D1, the light which has passed through the flow cell D1 without being scattered by the particles (blood cells or the like) is focused on the beam stopper S by the forward light focusing lens 201. The beam stopper S is configured by a thin plate member which is impenetrable to light. As shown in FIG. 3C, the beam stopper S has semicircular apertures S1 and S2, and a light shield S3 formed between the apertures S1 and S2. The width W1 in the width direction of the light shield S3 is constant. Direct light is focused on the light shield S3. As mentioned above, the beam shaping lens 103 converges the laser light so that the focus position of the laser light in the X-axis direction is in front (Z-axis negative direction) of the focus point of the laser light in the Y-axis direction. Therefore, the direct light is focused by the forward scattered light focusing lens 201 so that the focus position in the X-axis direction is in front (Z-axis negative direction) of the focus position in the Y-axis direction. The beam stopper S is arranged at the focus position of the direct light in the X-axis direction. The direct light therefore irradiates the light shield S3 as a long beam in the Y-axis direction, as shown in FIG. 3C.

The major part of the forward scattered light from the flow cell D1 passes through the apertures S1 and S2 of the beam stopper S, and part of the light is blocked by the light shield S3. The amount of forward scattered light blocked by the light shield S3 is determined by the width W1 of the light shield S3. The width W1 of the light shield S3 therefore is preferably as small as possible. However, the direct light can be reliably blocked by the light shield S3, and proper processing precision of the light shield S3 must be maintained. There is therefore a fixed limit to the reduction of the width W1 of the light shield S3. Normally, the width W1 is set at approximately 10 times the width of the direct light in the X-axis direction.

The side scattered light receiving optical system D5 is configured by a side light focusing lens D51, a dichroic mirror D52, and a photodiode D53. The scattered light (side scattered light) traveling from the flow cell D1 toward the side (X-axis positive direction) is focused by the side light focusing lens D51 and reflected by the dichroic mirror D52, and subsequently received by the photodiode D53. The photodiode 53 outputs electrical signals (side scattered light signals) corresponding to the intensity of the received side scattered light.

The fluorescent light receiving optical system D6 is configured by a spectral filter D61, and an avalanche photodiode D62. The fluorescent light traveling from the flow cell D1 toward the side (X-axis positive direction) is collected by the side focusing lens D51, passes through the dichroic mirror D52 and spectral filter D61, and reaches the avalanche photodiode D62. The avalanche photodiode D62 outputs electrical signals (fluorescent light signals) corresponding to the intensity of the received fluorescent light.

Returning now to FIG. 2, the forward scattered light signals, side scattered light signals, and fluorescent light signals obtained by the optical detector D are transmitted to the information processing unit 4. The information processing unit 4 performs analysis based on the received signals.

In the optical system shown in FIG. 3A, the forward light focusing lens 201 converts the forward scattered light passing through the central area to parallel rays, and converges the forward scattered light passing through the peripheral area. More specifically, the forward light focusing lens 201 is configured to convert the forward scattered light passing through the region from the optical axis of the forward light focusing lens 201 to a predetermined distance to parallel rays, and converge the forward scattered light passing through the peripheral area outside the central area. The diameter of the pinhole 202 is set to be somewhat larger than the diameter of the beam of parallel forward scattered light passing through the central area.

The amount of forward scattered light eliminated by the beam stopper S is reduced by the above described configuration of the forward light focusing lens 201.

Specific structural examples (examples) of the optical system provided with the forward light focusing lens 201 configured as described above, and the effectiveness of same are discussed below.

Examples

Figure 4A:
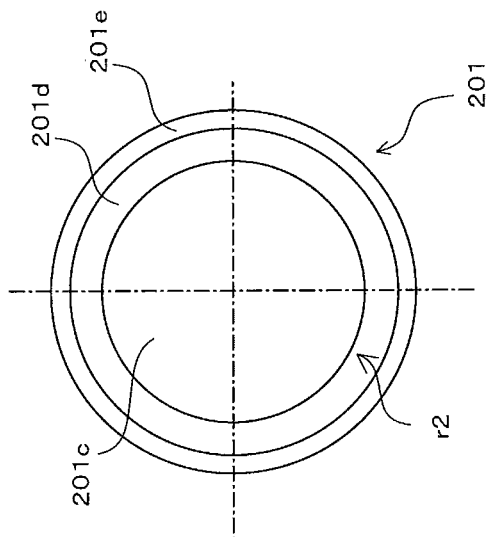
FIG. 4A views the forward light focusing lens 201 from the entrance surface r1 side.
Figure 4B:
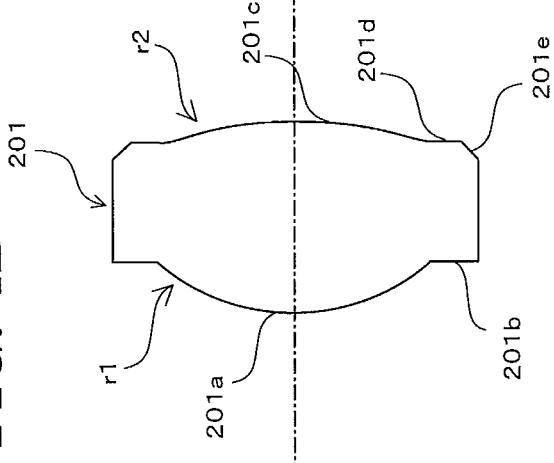
FIG. 4B shows the side surface of the forward light focusing lens.
Figure 4C:
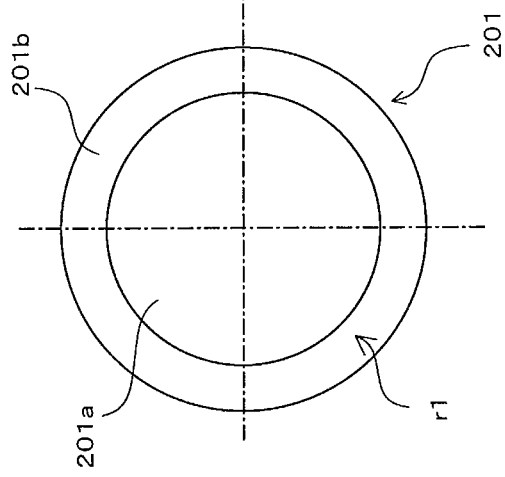
FIG. 4C views the forward light focusing lens from the exit surface side.

FIGS. 4A through 4C show the structure of a forward light focusing lens 201. FIG. 4A views the forward light focusing lens 201 from the entrance surface r1 side, FIG. 4B shows the side surface of the forward light focusing lens 201, and FIG. 4C views the forward light focusing lens 201 from the exit surface r2 side.

The entrance surface r1 of the forward light focusing lens 201 has a circular lens part 201a, and the flat part 201b on the periphery of the lens part 201a. The exit surface r2 of the forward light focusing lens 201 has a circular lens part 201c, and a flat part 201d and inclined part 201e on the periphery of the lens part 201c. In this example, the forward light focusing lens 201 is made of a plastic material.

FIG. 5 shows the structure of an optical system which includes the light irradiating optical system D3 and part of the forward scattered light receiving optical system D4 of the present example.

In the present example, a transparent optical path regulating member 104 is deployed to regulate the irradiation position of the laser light on the flow cell D1. The optical path regulating member 104 has an entrance surface and an exit surface which are perpendicular to the Z-axis. The optical path regulating member 104 changes the irradiation position of the laser light on the flow cell D1 to the X-axis direction or Y-axis direction by inclining in a direction parallel to the X-Z plane or a direction parallel to the Y-Z plane. Note that the optical path regulating member 104 may be omitted when suitable.

Although flow cell D1 is shown in FIG. 5 with the flow path D15 of the flow cell D1 parallel to the X-axis direction, the flow path D15 of the flow cell D1 is actually parallel to the Y-axis direction. FIG. 5 shows the emitter 101a and exit window 101b of the semiconductor laser 101.

FIGS. 6A and 6B respectively show the curvatures of the entrance surface r1 and exit surface r2 of the forward light focusing lens 201. FIGS. 6A and 6B respectively show the curvatures of the bottom sections, and the areas of the forward light focusing lens 201 and areas of the curvature shown in the lower stages are mutually associated. The horizontal axis in the graphs shown in the lower sections of FIGS. 6A and B represents the distance (mm) in the X-axis direction from the optical axis (center) of the forward light focusing lens 201, wherein the distance in the X-axis positive direction is positive, and the distance in the X-axis negative direction is negative. The vertical axis shown in the bottom sections of FIGS. 6A and 6B represent the curvature (reciprocal of the radius of curvature r). In FIG. 6A, the curvature in the projecting direction of the entrance surface r1 is positive, and in FIG. 6B the curvature in the projecting direction of the exit surface r2 is negative. Accordingly, the curvature in the projecting direction increases as the absolute value of the negative value increases in FIG. 6B. Note that although the curvature in the X-axis direction is shown in FIGS. 6A and 6B, the curvature in another direction around the optical axis similarly may be shown in the bottom sections of FIGS. 6A and 6B.

In FIG. 6A, A11 refers to the effective diameter of the entrance surface r1, and A12 refers to the incident area (hereinafter referred to as "focusing area") of the forward scattered light which is being focused. In FIG. 6B, A21 refers to the effective diameter of the exit surface r2, and A22 refers to the incident area (hereinafter referred to as "focusing region") of the forward scattered light being focused.

Referring to FIG. 6A, the entrance surface r1 has a maximum curvature at the optical axis (center) position, and the curvature gradually decreases according to the distance of the position in the X-axis direction in the focusing region A11 from the optical axis. The entrance surface r1 has an aspheric shape of monotonically changing curvature according to the distance of the position in the X-axis direction from the optical axis.

Referring to FIG. 6B, the exit surface r2 has a decreasing curvature near the optical axis, and the curvature increases in the peripheral area of the focusing area A22. The exit surface r2 has an unchanging curvature in the area A22 near the optical axis, and a gradually increasing curvature where the position in the X-axis direction exceeds area A22. Hence, the entrance surface r1 has an aspheric shape of variable curvature according to the position in the X-axis direction.

In the present example, the thickness of the forward light focusing lens 201 (that is, the distance from the entrance surface r1 on the optical axis to the exit surface r2) is set at 2.410 mm. The forward light focusing lens 201 may be formed, for example, from APEL5014DP (plastic), with a refractive index of 1.54.

According to this configuration, among the forward scattered light impinging the focusing area A1 of FIG. 6A, the forward scattered light passing through the area A23 of FIG. 6B is emitted from the exit surface r2 as parallel rays or diffused light. The border of the area A23 is a position 0.5 mm distant from the optical axis, and the rays of the forward scattered light passing through this position are parallel to the optical axis (parallel light rays). The forward scattered light passing through the area on the inner side of the border of the area S23 is diffused light somewhat spread from parallel. The forward scattered light passing through the area on the outer side of the border of the area A23 is convergent light.

FIG. 7A shows the condition of the forward scattered light focused by the forward light focusing lens 201, FIG. 7B is an enlargement of the vicinity of the photodiode 203, and FIG. 7C shows the condition of forward scattered light irradiation on the light receiving surface of the photodiode 203 when viewing the photodiode 203 from the Z-axis positive direction.

As shown in FIGS. 7A and B, in the present example the forward scattered light focused by the forward light focusing lens 201 is not convergent at a point, and the forward scattered light which passes through the central area is substantially parallel light due to the design of the forward light focusing lens 201. The forward scattered light therefore impinges the photodiode 203 while having a predetermined beam width. The diameter of the pinhole 202 is set somewhat larger than the beam width of the forward scattered light. As shown in FIG. 7C, the forward scattered light irradiates the light receiving surface while in a state with a certain degree of spreading on the light receiving surface of the photodiode 203.

The amount of forward scattered light eliminated by the beam stopper S is reduced by using the forward light focusing lens 201 of this example. The effectiveness of this example is compared with that of a comparative example below.

Figure 8:
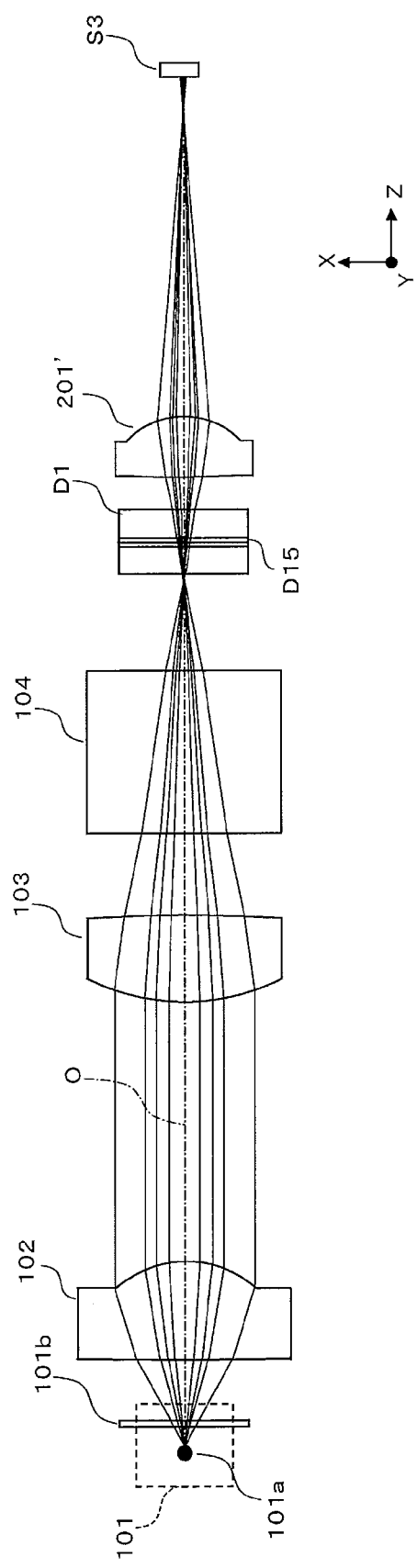
FIG. 8 shows the structures of the light irradiating optical system and the forward scattered light receiving optical system of a comparative example.

FIG. 8 shows the structure of the optical system of a comparative example.

In the comparative example, the forward light focusing lens 201' is an aspheric lens which converges the forward scattered light at a point.

Figure 9B:
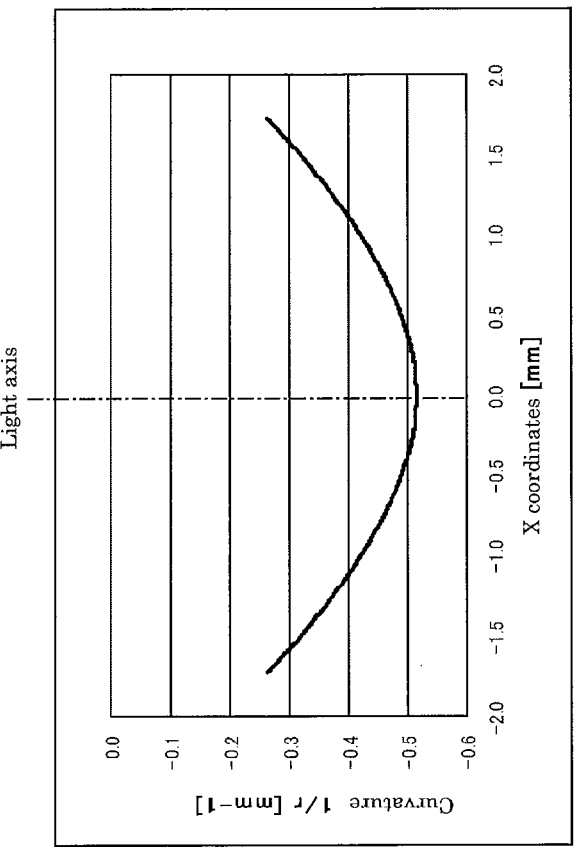
FIG. 9B shows the curvature of the exit surface of the forward light focusing lens.
Figure 9A:
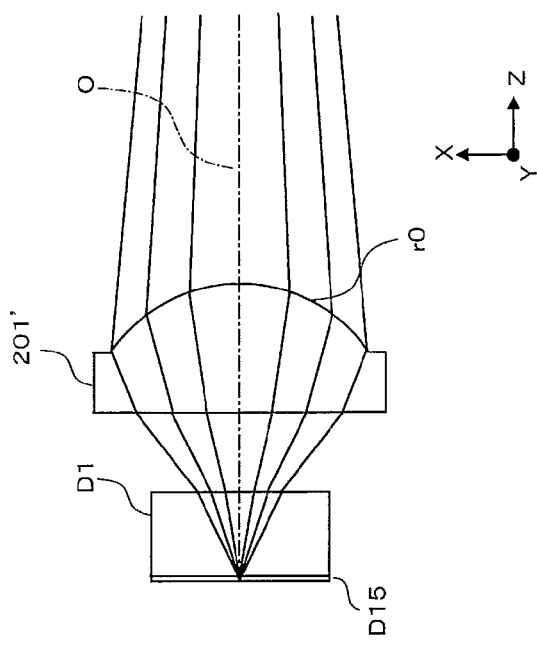
FIG. 9A illustrates the focus condition of the forward scattered light when using the forward light focusing lens of the comparative example.

FIG. 9A illustrates the focus condition of the forward scattered light when using the forward light focusing lens 201' of the comparative example, and FIG. 9B shows the curvature of the exit surface r0 of the forward light focusing lens 201'. In FIG. 9B, the curvature shown on the vertical axis is the curvature in the projection direction which increases with the increasing relative value of the negative value, similar to FIG. 6B.

As shown in FIG. 9B, the exit surface r0 of the forward light focusing lens 201' of the comparative example has a maximum curvature at the position of the optical axis (center), and the curvature gradually decreases with the distance of the position in the X-axis direction from the optical axis. The exit surface r0 has an aspherical shape of monotonically changing curvature according to the distance of the position in the X-axis direction from the optical axis.

As shown in FIG. 9A, the forward scattered light in the vicinity of the optical axis is also convergent when using the forward light focusing lens 201' of the comparative example.

Figure 10A:
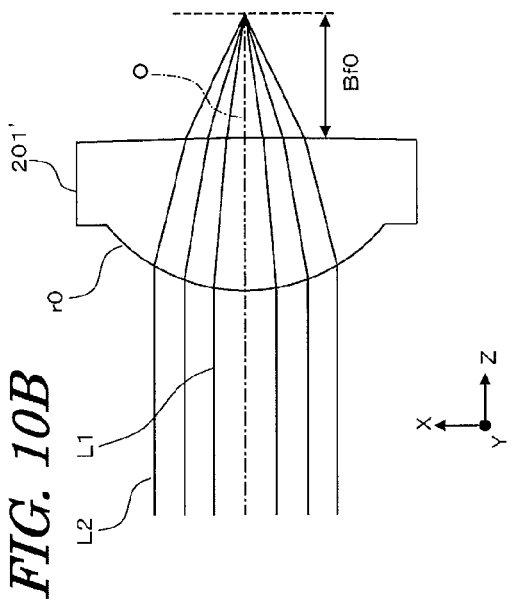
FIG. 10A shows the back focus of the forward light focusing lens of the example.
Figure 10B:
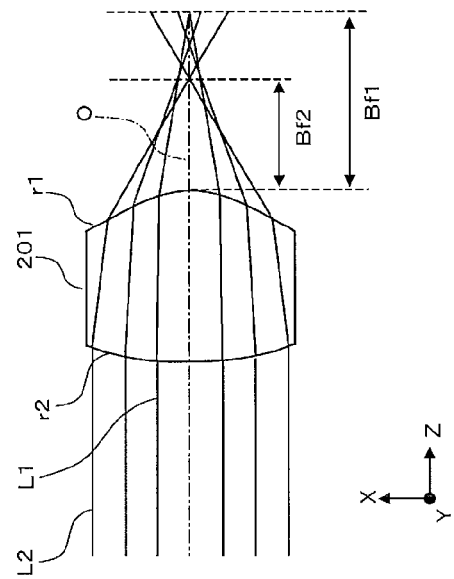
FIG. 10B show the back focus of the forward light focusing lens of the comparative example.

FIGS. 10A and 10B show the back focus of the forward light focusing lens 201 of the example and the forward light focusing lens 201' of the comparative example.

Referring to FIG. 10A, since the entrance surface r1 and the exit surface r2 have the above described configuration in the forward light focusing lens 201 of the example, the back focus Bf1 of the light rays (paraxial rays) L1 at a low angle through the vicinity of the optical axis is longer than the back focus Bf2 of the light rays (marginal rays) L2 at a wide angle through the outermost periphery. In contrast, in the forward light focusing lens 201' of the comparative example, the paraxial rays L1 at low angle through the vicinity of the optical axis and the marginal rays L2 at wide angle through the vicinity of the outermost periphery are convergent at substantially the same position, with the back focus Bf0 including virtually all light rays.

FIG. 11A shows the condition of the light rays passing through the vicinity of the edge of the light shield S3 of the beam stopper S when using the forward light focusing lens 201' of the comparative example, and FIG. 11B shows the condition of the light rays passing through the vicinity of the edge of the light shield S3 of the beam stopper S when using the forward light focusing lens 201 of the example.

In the forward light focusing lens 201' of the comparative example shown in FIG. 11A, the light rays passing through the vicinity of the optical axis easily reach the edge part of the light shield S3 because the forward scattered light passing through the vicinity of the optical axis is convergent, as mentioned above. In contrast, in the forward light focusing lens 201 of the example shown in FIG. 11B, the light rays passing through the vicinity of the optical axis are less likely to reach the edge part of the light shield S3 because the forward scattered light passing through the vicinity of the optical axis is diffused, as mentioned above. Simulations performed by the present inventors have shown that the angle of convergence (angle of inclination relative to the optical axis O) of the light rays passing near the edge of the light shield S3 was several degrees in the case of the comparative example. Conversely, the simulations also showed that the angle of convergence (angle of inclination relative to the optical axis O) of the light rays passing near the edge of the light shield S3 was 0.1 degrees in the case of the example.

When the forward light focusing lens 201 of the example is used, the amount of forward scattered light blocked by the edge part of the light shield S3 is reduced compared to the comparative example because the forward scattered light passing near the optical axis is parallel or diffused.

Figure 10C:
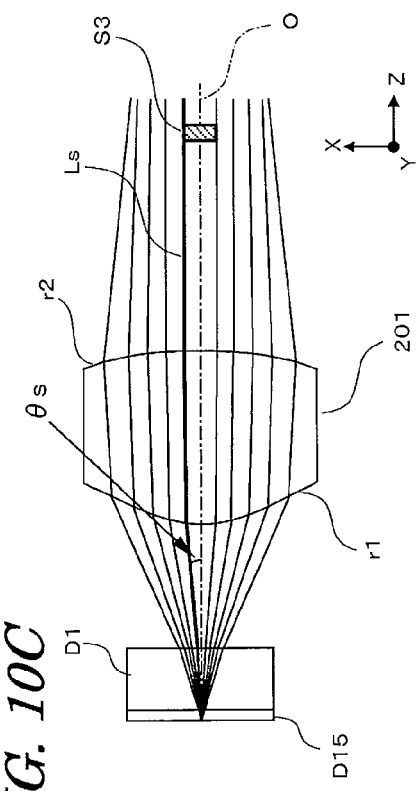
FIG. 10C shows the range of the forward scattered light blocked by the light shield.

FIG. 10C shows the range of the forward scattered light blocked by the light shield S3 at angle of inclination (hereinafter referred to as "light shielding angle") θs of the forward scattered light in the X-axis direction relative to the optical axis O.

The light shielding angle θs is defined as the angle formed by the optical axis O and the light rays Ls passing through the edge (furthermost edge) of the light shield S3 in the X-axis direction. When the optical axis O is through the center of the light shield S3, light rays, for which the angle of inclination in the X-axis positive direction relative to the optical axis O are within the range of the light shielding angle θs among the forward scattered light produced from the flow channel D15, impinge the light shield S3 and are blocked by the light shield S3. The light shielding angle θs is used as a standard value to evaluate the amount of forward scattered light blocked by the light shield S3. The present inventors used simulations to determine the light shielding angle θs when using the forward light focusing lens 201 of the example, and the light shielding angle θs when using the forward light focusing lens 201' of the comparative example. In these simulations the width W1 of the light shield S3 in the -axis direction (refer to FIG. 3) was set at 0.2 mm. The simulation results are shown below.

TABLE 1

| Light shielding angle (Example) | 2.01° |
|---|---|
| Light shielding angle (Comparative example) | 2.69° |

As can be understood from the simulation results, the light shielding angle θs becomes several steps smaller when using the forward light focusing lens 201 of the example than when using the forward light focusing lens 201' of the comparative example. Hence, the amount of forward scattered light blocked by the light shield S3 can be greatly reduced in the example compared to the comparative example.

According to the present example described above, since the forward light focusing lens 201 is configured to have the focal distance of the center part longer than the focal distance of the peripheral part, the travel direction of the light rays (forward scattered light) which have passed through the vicinity of the optical axis of the forward light focusing lens 201 is distanced from the optical axis O compared to the forward light focusing lens 201' of the comparative example which is configured to have the focal distance of the center part match the focal distance of the peripheral part. Therefore, the light rays (forward scattered light) which have passed near the optical axis are less likely to reach the light shield S3 of the beam stopper S and the amount of forward scattered light blocked by the beam stopper S is reduced compared to the comparative example. Therefore, the low angle scattered light can be received which cannot be received by the conventional configuration. Particle analysis can be performed with a higher level of accuracy by receiving the low angle scattered light because the low angle scattered light is strong compared to high angle scattered light. The optical system for receiving the low angle scattered light is easily adjustable to easily receive the low angle scattered light by using the forward light focusing lens 201 of the example. Even when the light shield S3 of the beam stopper S is wide, an increase in the amount of forward scattered light blocked by the light shield S3 can be suppressed. Therefore, processing errors of the beam stopper S can be reduced and dimensional variations suppressed by increasing the width of the light shield S3. Direct light from the light source can be reliably blocked and the position of the laser light can be easily adjusted relative to the optical axis by increasing the width of the light shield S3.

According to the present example, the construction costs of the forward light focusing lens 201 can be effectively reduced because the forward light focusing lens 201 can be configured by a plastic lens.

Although the present invention has been described by way of example and embodiments, the present invention is not limited to the embodiment.

For example, although the forward light focusing lens 201 is designed so that the forward scatter light passing near the border of the area A23 is parallel light and the forward scattered light passing on the inner side of the border of the area A23 is slightly diffused, the design of the forward light focusing lens 201 is not limited to this example. For example, the forward light focusing lens 201 also may be designed so that the forward scattered light passing within the area A23 is all parallel light, or the forward light focusing lens 201 may be designed so that the forward scattered light near the optical axis is somewhat diffused. How to set the area in which the forward scatter light is converted to substantially parallel light in the forward light focusing lens 201, and how to set the conditions of the forward scattered light in that area can be suitable set by considering both the effective reduction of the amount of forward scattered light impinging the light shield S3 of the beam stopper S, and reliable elimination of the of direct light by the light shield S3.

Figure 12:
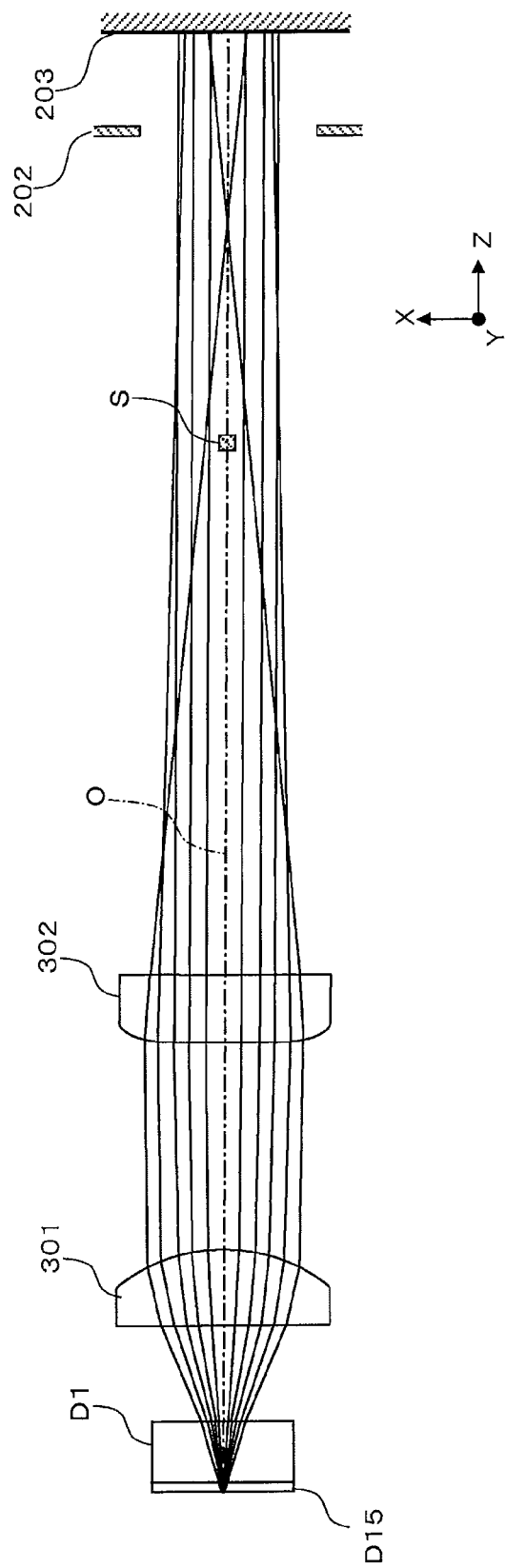
FIG. 12 shows the light receiving condition of the forward scattered light receiving optical system of a modification.

Although the above example has been described in terms of the forward scattered light from the particles flowing through the flow cell D1 being focused on the photodiode 203 by the single layer forward light focusing lens 201, the present invention is not limited to this example. A plurality of light focusing lenses also may be used to focus the forward scattered light on the photodiode 203. As shown in the modification of FIG. 12, for example, a light focusing lens system also may be used in which a spherical lens 301 is arranged on the flow cell side to convert the forward scattered light from the particles into parallel rays which are substantially parallel to the optical axis, and an aspheric lens 302 is arranged on the beam stopper S side to converge the high angle (outer side) forward scattered light more than the low angle (inner side) forward scattered light among the forward scattered light transmitted through the spherical lens 301. For example, the aspheric lens 302 may directly transmit the low angle (inner side) forward scattered light as substantially parallel rays, or converge with high angle (outer side) forward scattered light. Conversely, the low angle (inner side) forward scattered light may be somewhat converged or somewhat diffused. In this configuration, blocking the low angle forward scattered light from the particles also may be suppressed.

The present invention is not limited to these modifications inasmuch as a light focusing lens system may be used in which, for example, a first aspheric lens is arranged on the flow cell side to converge the forward scattered light from the particles at a point on the optical axis, and a second aspheric lens may be arranged on the beam stopper S side to convert the low angle forward scattered light to light substantially parallel to the optical axis or diffused light among the forward scattered light transmitted through the first aspheric lens. A light focusing lens system also may be used in which on the flow cell side is arranged a first aspheric lens which has a lens surface with the same curvature as the entrance surface r1 of the forward light focusing lens 201, and on the beam stopper S side is arranged a second aspheric lens which has a lens surface with the same curvature as the exit surface r2 of the forward light focusing lens 201. Note that each lens included in the light focusing lenses of these modifications also may be made of plastic materials.

Although the forward light focusing lens 201 the examples is made of plastic material, the present invention is not limited to these examples inasmuch as the forward light focusing lens 201 also may be formed of other materials such as glass material and the like.

Although a beam stopper S is arranged at a position to focus the direct light in the X-axis direction in the above examples, the beam stopper S also may be arranged at a position to focus the direct light in the Y-axis direction. In this case, the beam stopper S is arranged so that the longitudinal direction of the light shield S3 is parallel to the Y-axis direction.

Furthermore, a light source other than the semiconductor laser 101 may be used as the light source. The present invention may be variously and suitably modified within the range and technical scope stated in the claims.

The embodiments of the present invention may be variously modified insofar as such modifications are within the range of the technical ideas described in the scope of the claims.

What is claimed is:

1. A particle analyzer, comprising:
   a light source;
   a flow cell configured to flow a sample which includes particles;
   an irradiating optical system configured to irradiate light from the light source to a flow channel inside the flow cell; and
   a light receiving optical system configured to receive light from the flow channel,
   wherein the light receiving optical system comprises:
   a light focusing lens system which includes a light focusing lens configured to focus forward scattered light from the particles that flow in the flow channel;
   a light receiving member configured to receive the forward scattered light which is focused by the light focusing lens system; and
   a beam stopper configured to block direct light from the light source, wherein the beam stopper is provided in the light path between the light focusing lens system and the light receiving member,
   wherein the light focusing lens has an aspheric lens form,
   wherein the light focusing lens system is configured such that the focal distance of the forward scattered light through the central area of the light focusing lens which includes the optical axis is longer than the focal distance of the forward scattered light through the peripheral area of the light focusing lens outside the central area, and
   wherein the aspheric lens surface has a gradually increasing curvature toward the outer side in the peripheral area, and the central area has a smaller curvature than the peripheral area.

2. The particle analyzer of claim 1, wherein
   the light focusing lens system converges the forward scattered light passing through the peripheral area at a predetermined focal point, and converts the forward scattered light passing through the central area to parallel light or diffuse light.

3. The particle analyzer of claim 1, wherein
   the light focusing lens system is configured such that the focal distance of the central area is longer than the focal distance of the peripheral area, and one light focusing lens has an aspheric lens surface.

4. The particle analyzer of claim 1, wherein
   the aspheric lens surface has a substantially constant curvature in the area a predetermined distance from the light axis of the light focusing lens.

5. The particle analyzer of claim 1, wherein
   the light focusing lens is a plastic lens.

6. An optical system for a particle analyzer, comprising:
   an irradiating optical system configured to irradiate light from a light source to a flow channel in a flow cell through which a sample containing particles flows;
   a light receiving optical system configured to receive light from the flow cell;
   wherein the light receiving optical system comprises:
   a light focusing lens system which includes a light focusing lens configured to focus forward scattered light from the particles that flow in the flow channel;
   a light receiving member configured to receive the forward scattered light which is focused by the light focusing lens system; and a beam stopper configured to block direct light from the light source, wherein the beam stopper is provided in the light path between the light focusing lens system and the light receiving member, wherein the light focusing lens has an aspheric lens surface, the light focusing lens system is configured such that the focal distance of the forward scattered light through the central area of the light focusing lens which includes the optical axis is longer than the focal distance of the forward scattered light through the peripheral area of the light focusing lens outside the central area, and wherein the aspheric lens surface has a gradually increasing curvature toward the outer side in the peripheral area, and the central area has a smaller curvature than the peripheral area.

7. The optical system of the particle analyzer of claim 6, wherein the light focusing lens system converges the forward scattered light passing through the peripheral area at a predetermined focal point, and converts the forward scattered light passing through the central area to parallel light or diffuse light.

8. The optical system of the particle analyzer of claim 7, wherein the light focusing lens system is configured such that the focal distance of the central area is longer than the focal distance of the peripheral area, and one light focusing lens has an aspheric lens surface.

9. The optical system of the particle analyzer of claim 6, wherein the aspheric lens surface has a substantially constant curvature in the area a predetermined distance from the light axis of the light focusing lens.

10. The optical system of the particle analyzer of claim 6, wherein the light focusing lens is a plastic lens.

* * * * *